(12) United States Patent
Josso

(10) Patent No.: US 9,572,754 B2
(45) Date of Patent: *Feb. 21, 2017

(54) TRANSPARENT SELF-TANNING GELS CONTAINING A WATER-SOLUBLE/DISPERSIBLE ACRYLAMIDO-2-METHYLPROPANESULFONIC ACID POLYMER

(75) Inventor: Martin Josso, Paris (FR)

(73) Assignee: L'Oreal, Paris (FR)

( * ) Notice: Subject to any disclaimer, the term of this patent is extended or adjusted under 35 U.S.C. 154(b) by 2198 days.

This patent is subject to a terminal disclaimer.

(21) Appl. No.: 11/071,266

(22) Filed: Mar. 4, 2005

(65) Prior Publication Data
US 2005/0196364 A1    Sep. 8, 2005

Related U.S. Application Data

(60) Provisional application No. 60/587,063, filed on Jul. 13, 2004.

(30) Foreign Application Priority Data

Mar. 4, 2004 (FR) ...................................... 04 50439

(51) Int. Cl.
A61Q 19/04 (2006.01)
A61K 8/04 (2006.01)
A61K 8/81 (2006.01)

(52) U.S. Cl.
CPC ............. A61K 8/042 (2013.01); A61K 8/8158 (2013.01); A61Q 19/04 (2013.01); *A61K 2800/262* (2013.01)

(58) Field of Classification Search
USPC ...................................... 424/59, 60, 400, 401
See application file for complete search history.

(56) References Cited

U.S. PATENT DOCUMENTS

| | | | |
|---|---|---|---|
| 5,679,656 A | 10/1997 | Hansenne | |
| 6,120,780 A * | 9/2000 | Dupuis .................. | A61K 8/731 424/401 |
| 6,180,118 B1 | 1/2001 | Maubru | |
| 6,274,151 B1 | 8/2001 | Michel et al. | |
| 6,344,186 B1 * | 2/2002 | Hansenne et al. .............. | 424/60 |
| 6,399,679 B1 | 6/2002 | Meffert et al. | |
| 6,419,909 B1 * | 7/2002 | Lorant et al. ................... | 424/59 |
| 6,613,755 B2 | 9/2003 | Peterson et al. | |
| 6,905,674 B2 * | 6/2005 | L'Alloret ......................... | 424/59 |
| 8,216,554 B2 * | 7/2012 | Shah et al. ....................... | 424/59 |
| 2003/0059391 A1 * | 3/2003 | L'Alloret ................... | 424/70.11 |
| 2003/0147825 A1 * | 8/2003 | Chiarelli et al. ........... | 424/70.11 |
| 2003/0170196 A1 * | 9/2003 | Orsoni et al. .............. | 424/70.17 |
| 2003/0206955 A1 | 11/2003 | Sonneville-Aubrun et al. | |
| 2003/0235539 A1 * | 12/2003 | Mongiat et al. ................. | 424/59 |
| 2004/0228814 A1 * | 11/2004 | Candau ................... | A61K 8/585 424/59 |

FOREIGN PATENT DOCUMENTS

| | | | |
|---|---|---|---|
| AU | B-51855 | * 8/1997 | ............... A61K 7/42 |
| EP | 0 576 183 A1 | 12/1993 | |
| EP | 0 604 249 A1 | 6/1994 | |
| EP | 0 715 845 A1 | 6/1996 | |
| EP | 0 829 258 A1 | 3/1998 | |
| EP | 1 013 266 A1 | 6/2000 | |
| FR | 2 816 316 A1 | 5/2002 | |
| FR | 2 819 183 A1 | 7/2002 | |
| JP | 6-056629 A | 3/1994 | |
| JP | 6-199644 A | 7/1994 | |
| JP | 2000-063244 A | 2/2000 | |
| JP | 2000-191426 A | 7/2000 | |
| JP | 2001-335424 A | 12/2001 | |
| JP | 2003-073255 A | 3/2003 | |
| WO | 93/07856 A1 | 4/1993 | |

OTHER PUBLICATIONS

The report of National Industrial Chemicals Notification and Assessment Scheme, published on Oct. 21, 2002.*
Lubrizol, "AMPS 2405 monomer", <http://www.swt.co.kr/eng/pro_chem_lubr01.asp>, copyright 2003, p. 1-5.*
Seppic, "SIMULGEL™ NS, An emulsifying/thickening polymer . . . for New Sensations," published Jul. 2001, p. 1-41.*
National Industrial Chemicals Notification and Assessment Scheme (NICNAS), "Hydroxyethyl Acrylate/Sodium Acryloyldimethyl Taurate Copolymer," published Nov. 2, 2004, p. 1-8.*
Boutelet, et al., Compositions Autobronzantes a Base de Polymeres Amphiphiles d'Au Moins un Monomere a Insaturation Ethylenique a Groupement Sulfonique et Comportant Une Partie Hydrophobe, English abstract and machine-generated translation of FR2819183; Jul. 12, 2002.
Hansenne, et al., Compositions Containing Dihydroxyacetone and Their Cosmetic Use, English abstract and machine-generated translation of EP0604249; Jun. 29, 1994.
Kravtchenko, et al., Thickening Composition, Comprises a (Meth)Acrylamidoalkyl Sulfonic Acid Polymer and a Crosslinked Maleic Anhydride/Alkyl Vinyl Ether Copolymer, English abstract and machine-generated translation of FR2816316, May 10, 2002.

* cited by examiner

Primary Examiner — Tracy Vivlemore
Assistant Examiner — Monica Shin
(74) Attorney, Agent, or Firm — Buchanan Ingersoll & Rooney PC

(57) ABSTRACT

Topically applicable, stable, transparent self-tanning aqueous gels, suited for artificially tanning and/or browning human skin, contain at least one self-tanning agent and at least one water-soluble or water-dispersible, crosslinked or non-crosslinked (co)polymerizate of at least the acrylamido-2-methylpropanesulfonic acid (AMPS) monomer, or partially or totally neutralized form thereof, formulated into a topically applicable, cosmetically acceptable support therefor.

33 Claims, No Drawings

TRANSPARENT SELF-TANNING GELS CONTAINING A WATER-SOLUBLE/DISPERSIBLE ACRYLAMIDO-2-METHYLPROPANESULFONIC ACID POLYMER

CROSS-REFERENCE TO PRIORITY/PROVISIONAL APPLICATIONS

This application claims priority under 35 U.S.C. §119 of FR 04/50439, filed Mar. 4, 2004, and of provisional application Ser. No. 60/587,063, filed Jul. 13, 2004, each hereby expressly incorporated by reference and each assigned to the assignee hereof.

BACKGROUND OF THE INVENTION

Technical Field of the Invention

The present invention relates to transparent aqueous gels for topical application, which are suited for artificially tanning and/or browning the skin, and which comprise, formulated into a cosmetically acceptable support therefor, at least one monocarbonyl or polycarbonyl self-tanning agent and at least one water-soluble or water-dispersible, crosslinked or non-crosslinked polymer or copolymer polymerized from at least the acrylamido-2-methylpropanesulfonic acid (AMPS) monomer, in a form partially or totally neutralized with a mineral base other than ammonia.

The present invention also relates to a cosmetic treatment regime or regimen for artificially tanning and/or browning the skin, comprising topically applying thereon, for such period of time as required to elicit the desired effect, a thus effective amount of such a gel composition.

Description of Background and/or Related and/or Prior Art

It is known that monocarbonyl or polycarbonyl compounds, for instance isatin, alloxan, ninhydrin, glyceraldehyde, mesotartaric aldehyde, glutaraldehyde, erythrulose and dihydroxyacetone (DHA) are particularly advantageous products that are commonly included in cosmetics as agents for artificially tanning the skin.

When applied to the skin, especially to the face, these compounds make it possible to obtain a tanning or brown effect that is more or less similar in appearance to that which may result from prolonged exposure to sunlight (natural tanning) or under a UV light. Such a use also has the advantage of totally avoiding the risks of cutaneous reaction generally associated with the abovementioned prolonged exposures (erythemas, burns, loss of elasticity, appearance of wrinkles, premature aging of the skin, and the like).

Transparent cosmetic formulations are more and more appreciated by consumers for aesthetic reasons. Aqueous gels are particularly desired in cosmetics on account of their provision of water, which gives a pleasant sensation of freshness to the skin and due to the fact that they do not have a greasy appearance.

Transparent aqueous gels based on crosslinked acrylic polymers of the Carbomer type, for instance the Carbopol products from Noveon, may be obtained, but these gelling agents are incompatible with self-tanning agents such as dihydroxyacetone (DHA). Thickened aqueous formulations based on hydroxyethylcellulose and hydroxypropyl guar (Jaguar HP from Rhodia) may also be prepared. The products obtained have an unpleasant runny feel, are very tacky after application, and have poor stability over time. The use of cellulose derivatives as gelling agents gives transparent gels that have a tendency to peel on application.

Self-tanning aqueous gels containing a gelling agent of the polyacrylamide type are also described in WO 93/07856, especially Example II comprising dihydroxyacetone, the polyacrylamide/$C_{13}$-$C_{14}$ isoparaffin/laureth-7 mixture and benzyl alcohol. This type of composition does not allow transparent gels to be obtained.

An example of a transparent self-tanning gel containing polyacryloyidimethylammonium taurate polymer (crosslinked polymer of acrylamido-2-methylpropanesulfonic acid partially neutralized with ammonia, sold under the trademark Hostacerin AMPS) in combination with a copolymer of anhydride/alkyl vinyl ether (Stabileze QM), is also described in FR-2,816,316. This type of gel is not stable over time.

Need continues to exist for novel self-tanning compositions based on a monocarbonyl or polycarbonyl compound in the form of transparent aqueous gels, which do have the drawbacks indicated above and which have good cosmetic properties: non-runny feel, non-peeling, freshening effect, good stability over time and good self-tanning efficacy on the skin (intensity and staying power for the coloration).

SUMMARY OF THE INVENTION

It has now surprisingly and unexpectedly been found that it is possible to achieve these objectives by including a water-soluble or water-dispersible, crosslinked or non-crosslinked polymer or copolymer polymerized from at least the acrylamido-2-methylpropanesulfonic acid (AMPS) monomer, in free or in partially or totally neutralized form, in self-tanning gels.

The present invention thus features self-tanning transparent aqueous gels, comprising, formulated into cosmetically acceptable supports, therefor, at least one monocarbonyl or polycarbonyl self-tanning agent and at least one water-soluble or water-dispersible, crosslinked or non-crosslinked polymer or copolymer polymerized from at least the acrylamido-2-methylpropanesulfonic acid (AMPS) monomer, advantageously in a form partially or totally neutralized with a mineral base other than ammonia.

For the purposes of the present invention, the expression "artificial coloring of the skin" means a non-covering (non-opacifying) and long-lasting coloration that does not come off either with water or using a solvent, and which is resistant both to friction and to washing with a solution containing surfactants. Such a long-lasting, non-covering coloration is thus distinguished from the covering and temporary coloration provided, for example, by a makeup product.

The present invention also features a cosmetic treatment process (regime or regimen) for artificially tanning and/or browning the skin, comprising topically applying thereon a thus effective amount of such a composition.

DETAILED DESCRIPTION OF BEST MODE AND SPECIFIC/PREFERRED EMBODIMENTS OF THE INVENTION

The term "aqueous gel" means a composition containing a continuous aqueous phase containing a viscoelastic mass formed from colloidal suspensions. The viscosity of a gel according to the invention is measured at 25° C. using a Rheomat RM180 machine (rotor 2 or 3) from the company Rheometric Scientific, and its value is generally at least 60 DU (Deviation Units) with the rotor 2.

The term "transparent" means a composition having a turbidity of less than 400 NTU (Nephelometric Turbidity Units) at 25° C., and preferably less than 250 NTU at 25° C., measured using a 2100P Turbidimeter machine from the company Hach.

The gels in accordance with the present invention comprise an aqueous phase generally in a proportion of greater than or equal to 70% by weight, preferably greater than or equal to 80% by weight and more particularly greater than or equal to 90% by weight relative to the total weight of the gel.

The polymers formulated in accordance with the invention are crosslinked or non-crosslinked homopolymers or copolymers polymerized from at least the acrylamido-2-methylpropanesulfonic acid (AMPS) monomer, advantageously in a form partially or totally neutralized with a mineral base other than ammonia, such as sodium hydroxide or potassium hydroxide.

They are preferably totally neutralized or virtually totally neutralized, i.e., at least 90% neutralized.

These AMPS polymers according to the invention may be crosslinked or non-crosslinked.

When the polymers are crosslinked, the crosslinking agents may be selected from among the polyolefinically unsaturated compounds commonly used for the crosslinking of polymers obtained by free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allylic or vinyl ethers of polyfunctional alcohols, and also allylic esters of phosphoric and/or vinylphosphonic acid derivatives, or mixtures of these compounds.

According to one embodiment of the invention, the crosslinking agent is selected from among methylenebis-acrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The AMPS polymers in accordance with the invention are water-soluble or water-dispersible. In this case they are:
either "homopolymers" polymerized from only AMPS monomers and, if they are crosslinked, one or more crosslinking agents such as those defined above;
or copolymers polymerized from AMPS and from one or more hydrophilic or hydrophobic ethylenically unsaturated monomers and, if they are crosslinked, one or more crosslinking agents such as those defined above. When the said copolymers are polymerized from hydrophobic ethylenically unsaturated monomers, these monomers do not comprise a fatty chain and are preferably present in small amounts.

For the purposes of the present invention, the term "fatty chain" means any hydrocarbon-based chain containing at least 7 carbon atoms.

The term "water-soluble or water-dispersible" means polymers which, when introduced into an aqueous phase at 25° C., to a mass concentration equal to 1%, make it possible to obtain a macroscopically homogeneous and transparent solution, i.e., a solution that has a maximum light transmittance value, at a wavelength equal to 500 nm, through a sample 1 cm thick, of at least 60% and preferably of at least 70%.

The "homopolymers" according to the invention are preferably crosslinked and neutralized, and they may be prepared according to the preparation process comprising the following steps:
(a) the monomer such as AMPS in free form is dispersed or dissolved in a solution of tert-butanol or of water and tert-butanol;
(b) the solution or dispersion of monomer obtained in (a) is neutralized with one or more mineral or organic bases, preferably ammonia $NH_3$, in an amount making it possible to obtain a degree of neutralization of the sulfonic acid functions of the polymer ranging from 90% to 100%;
(c) the crosslinking monomer(s) is(are) added to the solution or dispersion obtained in (b);
(d) a standard free-radical polymerization is performed in the presence of free-radical initiators at a temperature ranging from 10 to 150° C.; the polymer precipitates in the solution or dispersion based on tert-butanol.

The water-soluble or water-dispersible AMPS copolymers according to the invention are polymerized from water-soluble ethylenically unsaturated monomers, hydrophobic monomers or mixtures thereof.

The water-soluble comonomers may be ionic or nonionic.

Among the ionic water-soluble comonomers, examples that may be mentioned include the following compounds and the salts thereof:
(meth)acrylic acid,
styrenesulfonic acid,
vinylsulfonic acid and (meth)allylsulfonic acid,
vinylphosphonic acid,
maleic acid,
itaconic acid,
crotonic acid,
the water-soluble vinyl monomers of formula (A) below:

in which:
$R_1$ is H, $-CH_3$, $-C_2H_5$ or $-C_3H_7$;
$X_1$ is selected from among:
alkyl ethers of $-OR_2$ type in which $R_2$ is a linear or branched, saturated or unsaturated hydrocarbon-based radical containing from 1 to 6 carbon atoms, substituted with at least one sulfonic ($-SO_3-$) and/or sulfate ($-SO_4-$) and/or phosphate ($-PO_4H_2-$) group.

Among the nonionic water-soluble comonomers, examples that may be mentioned include:
(meth)acrylamide,
N-vinylacetamide and N-methyl-N-vinylacetamide,
N-vinylformamide and N-methyl-N-vinylformamide,
maleic anhydride,
vinylamine,
N-vinyllactams comprising a cyclic alkyl group containing 4 to 9 carbon atoms, such as n-vinylpyrrolidone, N-butyrolactam and N-vinylcaprolactam,
vinyl alcohol of formula $CH_2$=CHOH, the water-soluble vinyl monomers of formula (B) below:

in which:
R$_{15}$ is H, —CH$_3$, —C$_2$H$_5$ or —C$_3$H$_7$;
X$_2$ is selected from among:
alkyl ethers of —OR$_{16}$ type in which R$_{16}$ is a linear or branched, saturated or unsaturated hydrocarbon-based radical containing from 1 to 6 carbons, optionally substituted with a halogen atom (iodine, bromine, chlorine or fluorine); a hydroxyl group (—OH); ether.

Mention is made, for example, of glycidyl (meth)acrylate, hydroxyethyl methacrylate and (meth)acrylates of ethylene glycol, of diethylene glycol or of polyalkylene glycol.

Among the fatty-chain-free hydrophobic comonomers, examples that may be mentioned include:
styrene and its derivatives, such as 4-butylstyrene, α-methylstyrene and vinyltoluene,
vinyl acetate of formula CH$_2$=CH—OCOCH$_3$;
vinyl ethers of formula CH$_2$=CHOR in which R is a linear or branched, saturated or unsaturated hydrocarbon-based radical containing from 1 to 6 carbons;
acrylonitrile,
caprolactone,
vinyl chloride and vinylidene chloride,
silicone derivatives, which provide silicone polymers after polymerization, such as methacryloxypropyltris(trimethylsiloxy)silane and silicone methacrylamides,
the hydrophobic vinyl monomers of formula (C) below:

in which:
R$_{23}$ is H, —CH$_3$, —C$_2$H$_5$ or —C$_3$H$_7$;
X$_3$ is selected from among:
alkyl ethers of —OR$_{24}$ type in which R$_{24}$ is a linear or branched, saturated or unsaturated hydrocarbon-based radical containing from 1 to 6 carbon atoms.

Mention is made, for example, of methyl methacrylate, ethyl methacrylate, n-butyl (meth)acrylate, tert-butyl (meth)acrylate, cyclohexyl acrylate and isobornyl acrylate and 2-ethylhexyl acrylate.

The water-soluble or water-dispersible AMPS polymers of the invention preferably have a molar mass ranging from 50,000 g/mol to 10,000,000 g/mol, preferably from 80,000 g/mol to 8,000,000 g/mol and even more preferably from 100,000 g/mol to 7,000,000 g/mol.

Examples of water-soluble or water-dispersible AMPS homopolymers in accordance with the invention that may be mentioned include crosslinked or non-crosslinked polymers of sodium acrylamido-2-methylpropanesulfonate, such as the polymer in the commercial product Simulgel 800 (CTFA name: Sodium Polyacryloyldimethyltaurate).

Examples of water-soluble or water-dispersible AMPS copolymers in accordance with the invention that may be mentioned include:

acrylamide/sodium acrylamido-2-methylpropanesulfonate crosslinked copolymers, such as the copolymer in the commercial product Sepigel 305 (CTFA name: Polyacrylamide/C$_{13}$-C$_{14}$ Isoparaffin/Laureth-7) or the copolymer in the commercial product sold under the trademark Simulgel 600 (CTFA name: Acrylamide/Sodium Acryloyldimethyltaurate/Isohexadecane/Polysorbate-80) by SEPPIC;

copolymers of AMPS and of vinylpyrrolidone or of vinylformamide, such as the copolymer in the commercial product sold under the name Aristoflex AVC by Clariant (CTFA name: Ammonium Acryloyldimethyltaurate/VP Copolymer) but neutralized with sodium hydroxide or potassium hydroxide;

copolymers of AMPS and of sodium acrylate, for instance AMPS/sodium acrylate copolymer such as the copolymer in the commercial product sold under the name Simulgel EG by SEPPIC (CTFA name: Acrylamide/Sodium Acryloyldimethyltaurate/Isohexadecane/Polysorbate-80);

copolymers of AMPS and of hydroxyethyl acrylate, for instance AMPS/hydroxyethyl acrylate copolymer, such as the copolymer in the commercial product sold under the name Simulgel NS by SEPPIC (CTFA name: Hydroxyethyl acrylate/Sodium Acryloyldimethyltaurate copolymer (and) Squalane (and) Polysorbate-60).

The preferred polymers are more particularly sodium acrylamido-2-methylpropanesulfonate homopolymers; such as the homopolymer in the commercial product Sepigel 800, and AMPS/hydroxyethyl acrylate copolymers, such as the copolymer in the commercial product sold under the name Simulgel NS.

According to one particularly preferred embodiment of the invention, the AMPS polymer or copolymer will be used in powder form.

The AMPS polymers in accordance with the invention are generally present in active material amounts ranging from 0.01% to 20% by weight, more preferably from 0.1% to 10% by weight, even more preferably from 0.1% to 5% by weight and even more particularly from 0.5% to 2% by weight relative to the total weight of the gel.

The monocarbonyl or polycarbonyl self-tanning agents are selected, for example, from among isatin, alloxan, ninhydrin, glyceraldehyde, mesotartaric aldehyde, glutaraldehyde, erythrulose, pyrazoline-4,5-dione derivatives as described in FR-2,466,492 and WO 97/35842, dihydroxyacetone (DHA) and 4,4-dihydroxypyrazolin-5-one derivatives as described in EP-A-0,903,342.

In one particularly preferred embodiment of the invention, dihydroxyacetone (DHA) will be used more particularly as self-tanning agent.

The self-tanning agents in accordance with the invention are generally present in the compositions in proportions ranging from 0.1% to 10% by weight relative to the total weight of the composition, and preferably from 0.2% to 8% by weight relative to the total weight of the composition.

The compositions in accordance with the invention may also contain other agents for artificially coloring the skin, among which mention may be made especially of:

(i) indole derivatives, for instance monohydroxyindoles, as described in FR-2,651,126 (i.e., 4-, 5-, 6- or 7-hydroxyindole) or dihydroxyindoles described in EP-B-0,425,324 (i.e., 5,6-dihydroxyindole, 2-methyl-5,6-dihydroxyindole, 3-methyl-5,6-dihydroxyindole or 2,3-dimethyl-5,6-dihydroxyindole);

(ii) plant extract agents for artificially coloring the skin, such as:

"insoluble" red wood extracts of the *Pterocarpus* genus and of the *Baphia* genus, for instance *Pterocarpus santalinus, Pterocarpus osun, Pterocarpus soyauxii, Pterocarpus erinaceus, Pterocarpus indicus* or *Baphia nitida*, such as those described in EP-A-0,971,683;

plant extracts of the *Saxifraga* genus, for instance *Saxifraga cuneifolia, Saxifraga glaucescens, Saxifraga rotundifolia, Saxifraga granulate, Saxifraga bulbifera, Saxifraga umbrosa* and *Saxifraga tridactylites;* plant extracts of the *Sorgho* genus, for instance *Sorghum caudatum* and *Sorghum bicolor;*

(iii) red or orange dyes of the fluorane type, for instance tetrabromofluoroscein or eosin (Cl 45380 or Red 21)

phloxin B (Cl 45410 or Red 27)

diiodofluorescein (Cl 45425 or Orange 10)

dibromofluorescein (Cl 45370 or Orange 5)

the sodium salt of tetrabromofluoroscein (Cl 45380 (Na salt) or Red 22)

the sodium salt of phloxin B (Cl 45410 (Na salt) or Red 28)

the sodium salt of diiodofluorescein (Cl 45425 (Na salt) or Orange 11)

erythrosine (Cl 45430 or Acid Red 51)

phloxin (Cl 45405 or Acid Red 98);

(iv) caramel.

The compositions may also contain a peptizer to promote the transparency of the composition. Mention may be made especially of decylglucosine, sold under the name "Oramix CG 110" by SEPPIC and hydrogenated oxyethylenated castor oil sold under the name "Cremophor RH 60" and "Cremophor RH 40" by BASF.

The composition may also additionally contain at least one UV-A-active and/or UV-B-active organic UV-screening agent; the said UV-screening agent may be water-soluble, liposoluble or insoluble in the cosmetic solvents commonly used.

The organic screening agents are selected especially from among anthranilates; cinnamic derivatives; dibenzoylmethane derivatives; salicylic derivatives; camphor derivatives; triazine derivatives such as those described in U.S. Pat. No. 4,367,390, EP-863,145, EP-517,104, EP-570,838, EP-796,851, EP-775,698, EP-878,469, EP-933,376, EP-507,691, EP-507,692, EP-790,243, EP-944,624; benzophenone derivatives; β,β-diphenylacrylate derivatives; benzotriazole derivatives; benzalmalonate derivatives; benzimidazole derivatives; imidazolines; bis-benzazolyl derivatives as described in EP-669,323 and U.S. Pat. No. 2,463,264; p-aminobenzoic acid (PABA) derivatives; benzoxazole derivatives as described in EP-0,832,642, EP-1,027,883, EP-1,300,137 and DE-101,62,844; methylenebis(hydroxyphenylbenzotriazole) derivatives as described in U.S. Pat. Nos. 5,237,071, 5,166,355, GB-2,303,549, DE-197,26,184 and EP-893,119; screening polymers and screening silicones such as those described especially in WO 93/04665; dimers derived from α-alkylstyrene, such as those described in DE-198,55,649; 4,4-diarylbutadienes such as those described in DE-197,55,649, EP-916,335, EP-1,133,980 and EP-1,133,981 and EP-A-1-008,586, and mixtures thereof.

As examples of UV-A-active and/or UV-B-active organic screening agents, mention may be made of those denoted hereinbelow under their INCI name:

para-Aminobenzoic Acid Derivatives:
PABA,
Ethyl PABA,
Ethyl dihydroxypropyl PABA,
Ethylhexyl dimethyl PABA sold in particular under the name "Escalol 507" by ISP,
Glyceryl PABA,
PEG-25 PABA sold under the name "Uvinul P25" by BASF.

Salicylic Derivatives:
Homosalate sold under the name "Eusolex HMS" by Rona/EM Industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.

Dibenzoylmethane Derivatives:
Butyl methoxydibenzoylmethane sold in particular under the trademark "Parsol 1789" by Hoffmann LaRoche,
Isopropyidibenzoylmethane.

Cinnamic Derivatives:
Ethylhexyl methoxycinnamate sold in particular under the trademark "Parsol MCX" by Hoffmann LaRoche,
Isopropyl methoxycinnamate,
Isoamyl methoxycinnamate sold under the trademark "Neo Heliopan E 1000" by Haarmann and Reimer,
Cinoxate,
DEA methoxycinnamate,
Diisopropyl methylcinnamate,
Glyceryl ethylhexanoate dimethoxycinnamate.

β,β-Diphenylacrylate Derivatives:
Octocrylene sold in particular under the trademark "Uvinul N539" by BASF,
Etocrylene sold in particular under the trademark "Uvinul N35" by BASF.

Benzophenone Derivatives:
Benzophenone-1 sold under the trademark "Uvinul 400" by BASF,
Benzophenone-2 sold under the trademark "Uvinul D50" by BASF,
Benzophenone-3 or Oxybenzone sold under the trademark "Uvinul M40" by BASF,
Benzophenone-4 sold under the trademark "Uvinul MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "Uvinul DS-49" by BASF,
Benzophenone-12,
n-Hexyl 2-(4-diethylamino-2-hydroxybenzoyl)benzoate.

Benzylidenecamphor Derivatives:
3-Benzylidenecamphor manufactured under the name— "Mexoryl SD" by Chimex,
4-Methylbenzylidenecamphor sold under the name— "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.

Phenylbenzimidazole Derivatives:
Phenylbenzimidazolesulfonic acid sold in particular under the trademark "Eusolex 232" by Merck,
Benzimidazilate sold under the trademark "Neo Heliopan AP" by Haarmann and Reimer.

Triazine Derivatives:
Anisotriazine sold under the trademark "Tinosorb S" by Ciba Geigy,
Ethylhexyltriazone sold in particular under the trademark "Uvinul T150" by BASF,
Diethylhexylbutamidotriazone sold under the trademark "Uvasorb HEB" by Sigma 3V,
2,4,6-Tris(diisobutyl 4'-aminobenzalmalonate)-s-triazine.
Phenylbenzotriazole Derivatives:
Drometrizole trisiloxane sold under the name "Silatrizole" by Rhodia Chimie,
Methylenebis(benzotriazolyl)tetramethylbutylphenol sold in solid form under the trademark "Mixxim BB/100" by Fairmount Chemical, or in micronized form as an aqueous dispersion under the trademark "Tinosorb M" by Ciba Specialty Chemicals.
Anthranilic Derivatives:
Menthyl anthranilate sold under the trademark "Neo Heliopan MA" by Haarmann and Reimer.
Imidazoline Derivatives:
Ethylhexyldimethoxybenzylidenedioxoimidazoline propionate.
Benzalmalonate Derivatives:
Polyorganosiloxane containing benzalmalonate functions sold under the trademark "Parsol SLX" by Hoffmann La Roche.
4,4-Diarylbutadiene Derivatives:
1,1-Dicarboxy(2',2'-dimethylpropyl)-4,4-diphenylbutadiene.
Benzoxazole Derivatives:
2,4-Bis[5-1(dimethylpropyl)benzoxazol-2-yl(4-phenyl)imino]-6-(2-ethylhexyl)imino-1,3,5-triazine sold under the name Uvasorb K2A by Sigma 3V,
and mixtures thereof.

The organic UV-screening agents that are more particularly preferred are selected from among the following compounds:
Ethylhexyl salicylate,
Butyl methoxydibenzoylmethane,
Ethylhexyl methoxycinnamate,
Octocrylene,
Phenylbenzimidazolesulfonic acid,
Terephthalylidenedicamphorsulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Benzimidazilate,
Anisotriazine,
Ethylhexyltriazone,
Diethylhexylbutamidotriazone,
2,4,6-Tris(diisobutyl 4'-aminobenzalmalonate)-s-triazine,
Methylenebis(benzotriazolyl)tetramethylbutylphenol,
Drometrizole trisiloxane,
Polysilicone-15
1,1-Dicarboxy(2',2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine
and mixtures thereof.

The UV-screening agents in accordance with the invention are generally present in the gels according to the invention in proportions ranging from 0.1% to 20% by weight and preferably ranging from 0.2% to 15% by weight relative to the total weight of the gel.

The gels in accordance with the present invention may also comprise standard cosmetic adjuvants and additives selected especially from among fatty substances, organic solvents, ionic or nonionic thickeners, softeners, antioxidants, free-radical scavengers, stabilizers, sequestering agents, emollients, silicones, α-hydroxy acids, antifoams, moisturizers, vitamins, insect repellents, fragrances, preservatives, surfactants, anti-inflammatory agents, substance P antagonists, fillers, polymers, propellants, acidifying or basifying agents, dyes or any other ingredient usually used in cosmetics and/or dermatology, in particular for the manufacture of compositions in the form of transparent aqueous gels.

The fatty substances may be an oil or mixtures of oils. The term "oil" means a compound that is liquid at room temperature.

Oils that may be mentioned include mineral oils (paraffin); plant oils (sweet almond oil, macadamia oil, blackcurrant seed oil or jojoba oil); synthetic oils, for instance perhydrosqualene, fatty alcohols, fatty acids or fatty esters (for instance the $C_{12}$-$C_{15}$ alkyl benzoate sold under the trademark "Finsolv TN" by Finetex, octyl palmitate, isopropyl lanolate, triglycerides, including capric/caprylic acid triglycerides), oxyethylenated or oxypropylenated fatty esters and ethers; silicone oils (cyclomethicone, polydimethylsiloxanes or PDMS) or fluoro oils, and polyalkylenes.

The aqueous phase of the subject compositions contains water and, in general, other water-soluble or water-miscible solvents. The water-soluble or water-miscible solvents comprise short-chain monoalcohols, for example of $C_1$-$C_4$, for instance ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol and glycerol will be used more particularly.

Needless to say, one skilled in this art will take care to select the optional additional compound(s) mentioned above and/or the amounts thereof such that the advantageous properties intrinsically associated with the invention are not, or are not substantially, adversely affected by the envisaged addition(s).

This invention also features the use of this aqueous gel for the manufacture of a product for artificially coloring the skin.

The invention also features a cosmetic treatment regime or regimen for artificially tanning and/or browning the skin, comprising topically applying thereon a thus effective amount of a composition as defined above.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

In all of the examples below:
the viscosity was measured at 25° C. using a Rheomat RM180 machine from the company Rheometric Scientific, with a rotor 3; it is expressed in EU (Deviation Units);
the turbidity was measured at 25° C. using a 2100P Turbidimeter machine from the company Hach; it is expressed in NTU (Neophelometric Turbidity Units).

Example 1

Transparent Self-Tanning Gel

| | |
|---|---|
| Dihydroxyacetone | 5.0% by weight |
| Decylglucoside (Oramix CG 110) | 1.5% by weight |
| Sodium polyacryloyldimethyltaurate in powder form (MP 6123 from SEPPIC, derived from Simulgel 800) | 1.0% by weight |
| Purified water | 92.5% by weight |
| Turbidity 5 NTU at 25° C. | |
| Viscosity 40 DU (rotor 3) at 25° C. | |
| pH 5 | |

Example 2

Transparent Self-Tanning Gel

| | |
|---|---|
| Dihydroxyacetone | 5.0% by weight |
| Decylglucoside (Oramix CG 110) | 1.5% by weight |
| Hydroxyethyl acrylate/sodium acryloyldimethyltaurate Copolymer in powder form (MP 5955 from SEPPIC, derived from Simulgel NS) | 1.0% by weight |
| Purified water | 92.5% by weight |
| Turbidity 5 NTU at 25° C. | |
| Viscosity 25 DU (rotor 3) at 25° C. | |
| pH 5 | |

Example 3

Transparent Self-Tanning Gel

| | |
|---|---|
| Dihydroxyacetone | 5.0% by weight |
| Hydrogenated oxyethylenated castor oil (60 EO) (Cremophor RH 60 from BASF) | 1.5% by weight |
| Sodium polyacryloyldimethyltaurate in powder form (MP 6123 from SEPPIC, derived from Simulgel 800) | 1.0% by weight |
| Purified water | 92.5% by weight |
| Turbidity 87 NTU at 25° C. | |
| Viscosity 53 DU (rotor 3) at 25° C. | |
| pH 5 | |

Example 4

Transparent Self-Tanning Gel

| | |
|---|---|
| Dihydroxyacetone | 5.0% by weight |
| Hydrogenated oxyethylenated castor oil (60 EO) (Cremophor RH 60 from BASF) | 2.0% by weight |
| Sodium polyacryloyldimethyltaurate in powder form (MP 6123 from SEPPIC, derived from Simulgel 800) | 1.0% by weight |
| DL-α-Tocopherol (vitamin E) | 0.1% by weight |
| Glycerol | 5.0% by weight |
| Propylene glycol | 5.0% by weight |
| Fragrance | 0.3% by weight |
| Purified water | 81.6% by weight |
| Turbidity 218 NTU at 25° C. | |
| Viscosity 58 DU (rotor 3) at 25° C. | |
| pH 5.4 | |

Example 5

Comparative

Opaque self-tanning gel according to WO 93/07856 Example II page 12

| | |
|---|---|
| Dihydroxyacetone | 3.0% by weight |
| Polyacrylamide/$C_{13}$–$C_{14}$ isoparaffin/laureth-7 (Sepigel 305 from SEPPIC) | 3.0% by weight |
| Benzyl alcohol | 0.5% by weight |
| Purified water | 93.5% by weight |
| Turbidity > 1000 NTU at 25° C. | |
| Viscosity 90 DU (rotor 3) at 25° C. | |
| pH 5.8 | |

The gel obtained is not transparent.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, cosmetically acceptable, stable, transparent self-tanning aqueous gel, suited for artificially tanning and/or browning human skin, comprising at least one monocarbonyl or polycarbonyl self-tanning agent and at least one water-soluble or water-dispersible, non-crosslinked copolymer comprising at least an acrylamido-2-methylpropanesulfonic acid monomer, in a form partially or totally neutralized with a mineral base other than ammonia, said copolymer being selected from the group consisting of:
   (i) copolymers formed from an acrylamido-2-methylpropanesulfonic acid monomer and vinylpyrrolidone or vinylformamide;
   (ii) copolymers formed from an acrylamido-2-methylpropanesulfonic acid monomer and sodium acrylate; and
   (iii) copolymers formed from an acrylamido-2-methylpropanesulfonic acid monomer and hydroxyethyl acrylate;
   formulated into a topically applicable, cosmetically acceptable support;
   said gel having a turbidity of less than 400 NTU.

2. The transparent self-tanning aqueous gel as defined by claim 1, comprising at least 70% by weight of an aqueous phase.

3. The transparent self-tanning aqueous gel as defined by claim 1, comprising at least 80% by weight of an aqueous phase.

4. A topically applicable, cosmetically acceptable, stable, transparent self-tanning aqueous gel, suited for artificially tanning and/or browning human skin, comprising at least one monocarbonyl or polycarbonyl self-tanning agent and at least one water-soluble or water-dispersible, non-crosslinked copolymer comprising at least an acrylamido-2-methylpropanesulfonic acid monomer, in a form partially or totally neutralized with a mineral base other than ammonia, said copolymer being selected from the group consisting of:
   (i) copolymers formed from an acrylamido-2-methylpropanesulfonic acid monomer and vinylpyrrolidone or vinylformamide;

(ii) copolymers formed from an acrylamido-2-methylpropanesulfonic acid monomer and sodium acrylate; and
(iii) copolymers formed from an acrylamido-2-methylpropanesulfonic acid monomer and hydroxyethyl acrylate;
formulated into a topically applicable, cosmetically acceptable support;
said gel having a turbidity of less than 400 NTU;
wherein the aqueous gel comprises at least 90% by weight of an aqueous phase.

5. The transparent self-tanning aqueous gel as defined by claim 1, said at least one copolymer being at least 90% neutralized.

6. The transparent self-tanning aqueous gel as defined by claim 1, said at least one water-soluble or water-dispersible copolymer having a molar mass ranging from 50,000 g/mol to 10,000,000 g/mol.

7. The transparent self-tanning aqueous gel as defined by claim 1, wherein said at least one water-soluble or water-dispersible copolymer is a copolymer formed from an acrylamido-2-methylpropanesulfonic acid monomer and hydroxyethyl acrylate.

8. The transparent self-tanning aqueous gel as defined by claim 1, comprising from 0.01% to 20% by weight of said at least one water-soluble or water-dispersible copolymer.

9. The transparent self-tanning aqueous gel as defined by claim 1, said at least one monocarbonyl or polycarbonyl self-tanning agent being selected from the group consisting of isatin, alloxan, ninhydrin, glyceraldehyde, mesotartaric aldehyde, glutaraldehyde, erythrulose, pyrazoline-4,5-dione derivatives, dihydroxyacetone (DHA) and 4,4-dihydroxypyrazolin-5-one compounds.

10. The transparent self-tanning aqueous gel as defined by claim 9, said at least one monocarbonyl or polycarbonyl self-tanning agent comprising dihydroxyacetone (DHA).

11. The transparent self-tanning aqueous gel as defined by claim 1, comprising from 0.1% to 10% by weight of said at least one self-tanning agent.

12. The transparent self-tanning aqueous gel as defined by claim 1, said at least one water-soluble or water-dispersible copolymer being at least 90% neutralized with sodium hydroxide.

13. A topically applicable, cosmetically acceptable, stable, transparent self-tanning aqueous gel, suited for artificially tanning and/or browning human skin, consisting essentially of at least one monocarbonyl or polycarbonyl self-tanning agent and at least one water-soluble or water-dispersible, non-crosslinked copolymer of at least an acrylamido-2-methylpropanesulfonic acid (AMPS) monomer, in a form partially or totally neutralized with a mineral base other than ammonia, said copolymer being selected from the group consisting of:
(i) copolymers formed from an acrylamido-2-methylpropanesulfonic acid monomer and vinylpyrrolidone or vinylformamide;
(ii) copolymers formed from an acrylamido-2-methylpropanesulfonic acid monomer and sodium acrylate; and
(iii) copolymers formed from an acrylamido-2-methylpropanesulfonic acid monomer and hydroxyethyl acrylate;
formulated into a topically applicable, cosmetically acceptable support;
said gel having a turbidity of less than 400 NTU.

14. The transparent self-tanning aqueous gel as defined by claim 13, said at least one water-soluble or water-dispersible copolymer being at least 90% neutralized with sodium hydroxide.

15. The transparent self-tanning aqueous gel as defined by claim 1, further comprising at least one peptizer.

16. The transparent self-tanning aqueous gel as defined by claim 15, said at least one peptizer comprising decylglucosine or hydrogenated oxyethylenated castor oil.

17. The transparent self-tanning aqueous gel as defined by claim 1, further comprising at least one UV-A- and/or UV-B-organic UV-screening agent.

18. The transparent self-tanning aqueous gel as defined by claim 17, said at least one organic UV-screening agent being selected from the group consisting of anthranilates; cinnamic derivatives; dibenzoylmethane derivatives; salicylic derivatives; camphor derivatives; triazine derivatives; benzophenone derivatives; $\beta,\beta$-diphenylacrylate derivatives; benzotriazole derivatives; benzalmalonate derivatives; benzimidazole derivatives; imidazolines; bis-benzazolyl derivatives; p-aminobenzoic acid (PABA) derivatives; benzoxazole derivatives; methylenebis (hydroxyphenylbenzotriazole) derivatives; screening polymers and screening silicones; dimers derived from $\alpha$-alkylstyrene; 4,4-diarylbutadienes, and mixtures thereof.

19. The transparent self-tanning aqueous gel as defined by claim 18, said at least one organic UV-screening agent being selected from the group consisting of:
Ethylhexyl salicylate,
Butyl methoxydibenzoylmethane,
Ethylhexyl methoxycinnamate,
Octocrylene,
Phenylbenzimidazolesulfonic acid,
Terephthalylidenedicamphorsulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Benzimidazilate,
Anisotriazine,
Ethylhexyltriazone,
Diethylhexylbutamidotriazone,
2,4,6-Tris(diisobutyl 4'-aminobenzalmalonate)-s-triazine,
Methylenebis(benzotriazolyl)tetramethylbutylphenol,
Drometrizole trisiloxane,
Polysilicone-15,
1,1-Dicarboxy(2',2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine,
and mixtures thereof.

20. The transparent self-tanning aqueous gel as defined by claim 17, comprising from 0.1% to 20% by weight of said at least one organic UV-screening agent.

21. The transparent self-tanning aqueous gel as defined by claim 1, further comprising at least one cosmetic additive or adjuvant selected from the group consisting of fatty substances, organic solvents, ionic thickeners, nonionic thickeners, softeners, antioxidants, free-radical scavengers, stabilizers, sequestering agents, emollients, silicones, $\alpha$-hydroxy acids, antifoams, moisturizers, vitamins, insect repellents, fragrances, preservatives, surfactants, anti-inflammatory agents, substance P antagonists, fillers, polymers, propellants, acidifying agents, basifying agents and dyes.

22. A method for artificially tanning and/or browning human skin, comprising topically applying thereon, for such period of time as required to elicit the desired effect, a thus effective amount of a topically applicable, cosmetically acceptable, stable, transparent self-tanning aqueous gel which comprises at least one monocarbonyl or polycarbonyl self-tanning agent and at least one water-soluble or water-dispersible, non-crosslinked copolymer of at least an acrylamido-2-methylpropanesulfonic acid monomer, in a form partially or totally neutralized with a mineral base other than ammonia, said copolymer being selected from the group consisting of:
(i) copolymers formed from an acrylamido-2-methylpropanesulfonic acid monomer and vinylpyrrolidone or vinylformamide;
(ii) copolymers formed from an acrylamido-2-methylpropanesulfonic acid monomer and sodium acrylate; and
(iii) copolymers formed from an acrylamido-2-methylpropanesulfonic acid monomer and hydroxyethyl acrylate;
formulated into a topically applicable, cosmetically acceptable support;
said gel having a turbidity of less than 400 NTU.

23. A method for artificially tanning and/or browning human skin, which consists essentially of topically applying thereon, for such period of time as required to elicit the desired effect, a thus effective amount of a topically applicable, cosmetically acceptable, stable, transparent self-tanning aqueous gel which comprises at least one monocarbonyl or polycarbonyl self-tanning agent and at least one water-soluble or water-dispersible, non-crosslinked copolymer of at least an acrylamido-2-methylpropanesulfonic acid monomer, in a form partially or totally neutralized with a mineral base other than ammonia, said copolymer being selected from the group consisting of:
(i) copolymers formed from an acrylamido-2-methylpropanesulfonic acid monomer and vinylpyrrolidone or vinylformamide;
(ii) copolymers formed from an acrylamido-2-methylpropanesulfonic acid monomer and sodium acrylate; and
(iii) copolymers formed from an acrylamido-2-methylpropanesulfonic acid monomer and hydroxyethyl acrylate;
formulated into a topically applicable, cosmetically acceptable support;
said gel having a turbidity of less than 400 NTU.

24. The transparent self-tanning aqueous gel as defined by claim 1, wherein said at least one water-soluble or water-dispersible copolymer further comprises sodium polyacryloyldimethyltaurate.

25. The transparent self-tanning aqueous gel as defined by claim 1, wherein said at least one water-soluble or water-dispersible copolymer further comprises a copolymer of an acrylamido-2-methylpropanesulfonic acid monomer and acrylamide/sodium acryloyldimethyltaurate.

26. The transparent self-tanning aqueous gel as defined by claim 13, wherein the copolymer is selected from the group consisting of:
(iii) copolymers formed from an acrylamido-2-methylpropanesulfonic acid monomer and hydroxyethyl acrylate.

27. The method as defined by claim 22, wherein the copolymer is selected from the group consisting of:
(iii) copolymers formed from an acrylamido-2-methylpropanesulfonic acid monomer and hydroxyethyl acrylate.

28. The method as defined by claim 23, wherein the copolymer is selected from the group consisting of:
(iii) copolymers formed from an acrylamido-2-methylpropanesulfonic acid monomer and hydroxyethyl acrylate.

29. The transparent self-tanning aqueous gel as defined by claim 1, wherein the copolymer is selected from the group consisting of:
(ii) copolymers formed from an acrylamido-2-methylpropanesulfonic acid monomer and sodium acrylate; and
(iii) copolymers formed from an acrylamido-2-methylpropanesulfonic acid monomer and hydroxyethyl acrylate.

30. The transparent self-tanning aqueous gel as defined by claim 13, wherein the copolymer is selected from the group consisting of:
(ii) copolymers formed from an acrylamido-2-methylpropanesulfonic acid monomer and sodium acrylate; and
(iii) copolymers formed from an acrylamido-2-methylpropanesulfonic acid monomer and hydroxyethyl acrylate.

31. The method as defined by claim 22, wherein the copolymer is selected from the group consisting of:
(ii) copolymers formed from an acrylamido-2-methylpropanesulfonic acid monomer and sodium acrylate; and
(iii) copolymers formed from an acrylamido-2-methylpropanesulfonic acid monomer and hydroxyethyl acrylate.

32. The method as defined by claim 23, wherein the copolymer is selected from the group consisting of:
(ii) copolymers formed from an acrylamido-2-methylpropanesulfonic acid monomer and sodium acrylate; and
(iii) copolymers formed from an acrylamido-2-methylpropanesulfonic acid monomer and hydroxyethyl acrylate.

33. The transparent self-tanning aqueous gel as defined by claim 1, comprising from 0.5% to 2% by weight of said at least one water-soluble or water-dispersible copolymer, and wherein said gel has a turbidity of less than 250 NTU.

* * * * *